United States Patent
Beigelman et al.

(10) Patent No.: US 6,509,460 B1
(45) Date of Patent: Jan. 21, 2003

(54) NUCLEOSIDE TRIPHOSPHATES AND THEIR INCORPORATION INTO OLIGONUCLEOTIDES

(75) Inventors: Leonid Beigelman, Longmont, CO (US); Alex Burgin, Chula Vista, CA (US); Amber Beaudry, Broomfield, CO (US); Alexander Karpeisky, Lafayette, CO (US); Jasenka Matulic-Adamic, Boulder, CO (US); David Sweedler, Louisville, CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 26 days.

(21) Appl. No.: 09/644,966

(22) Filed: Aug. 23, 2000

Related U.S. Application Data

(63) Continuation of application No. 09/186,675, filed on Nov. 4, 1998, now Pat. No. 6,127,535.
(60) Provisional application No. 60/064,866, filed on Nov. 5, 1997.

(51) Int. Cl.[7] .......................... C07H 19/10; C07H 19/20
(52) U.S. Cl. .............................. 536/26.26; 536/237.1; 536/25.3; 536/24.3; 435/6; 435/91.31; 435/179; 435/366; 514/44
(58) Field of Search .............................. 536/26.26, 23.1, 536/25.3, 24.3; 435/6, 91.31, 179, 366; 514/44

(56) References Cited

U.S. PATENT DOCUMENTS

| | | |
|---|---|---|
| 5,591,721 A | 1/1997 | Agrawal et al. |
| 5,616,459 A | 4/1997 | Kramer et al. |
| 5,652,356 A | 7/1997 | Agrawal |
| 5,691,141 A * | 11/1997 | Koster et al. .................. 435/6 |
| 5,840,876 A * | 11/1998 | Beigelman et al. ......... 536/25.3 |
| 6,127,535 A * | 10/2000 | Beigelman et al. ....... 536/26.26 |

FOREIGN PATENT DOCUMENTS

| | | |
|---|---|---|
| DE | 44 24 762 C1 | 7/1995 |
| WO | 92/07065 | 4/1992 |
| WO | 93/15187 | 5/1993 |
| WO | 93/23057 | 11/1993 |
| WO | 93/23569 | 11/1993 |
| WO | 94/02595 | 2/1994 |
| WO | 95/11910 | 5/1995 |
| WO | 95/13378 | 5/1995 |
| WO | 95/23225 | 8/1995 |
| WO | 95/35102 | 12/1995 |
| WO | 96/10390 | 4/1996 |
| WO | 96/10391 | 4/1996 |
| WO | 96/10392 | 4/1996 |
| WO | 96/18736 | 6/1996 |
| WO | 98/32880 | 7/1998 |

OTHER PUBLICATIONS

Aurup et al., "2–Fluoro– and 2′–amino–2′–deoxynucleoside 5′–triphosphates as substrates for T7 RNA polymerase," *Biochemistry* 31:9636–9641 (Issue No. 40, Oct. 13, 1992).
Bartel and Szostak, "Isolation of New Ribozymes From a Large Pool of Random Sequences," *Science* 261:1411–1418 (Sep. 10, 1993).

(List continued on next page.)

*Primary Examiner*—Samuel Barts
*Assistant Examiner*—Devesh Khare
(74) *Attorney, Agent, or Firm*—McDonnell Boehnen Hulbert & Berghoff

(57) ABSTRACT

Novel nucleoside triphosphates, methods of synthesis and process of incorporating these nucleoside triphosphates into oligonucleotides are disclosed.

12 Claims, 1 Drawing Sheet

OTHER PUBLICATIONS

Beaudry and Joyce, "Directed Evolution of an RNA Enzyme," *Science* 257:635–641 (Jul. 31, 1992).

Bonner et al., "Characterization of a set of T7 RNA polymerase active site mutants," *J. Biol. Chem.* 269:25120–25128 (Issue No. 40, Oct. 7, 1994).

Breaker and Joyce, "Inventing and improving ribozyme function: rational design versus iterative selection methods," *TIBTECH* 12:268–275 (Jul., 1994).

Breaker, "Are engineered proteins getting competition from RNA?" *Current Opinion in Biotechnology* 7:442–448 (1996).

Brenner et al., "Encoded combinatorial chemistry," *Proc. Natl. Acad. Sci.* 89:5381–5383 (Jun. 15, 1992) (Issue No. 12).

Burgin et al., "Chemically Modified Hammerhead Ribozymes with Improved Catalytic Rates," *Biochemistry* 35:14090–14097 (1996) (Issue No. 45).

Cotton, "The in vivo application of ribozymes," *TIBS* 8 (7): 174–178 (1990).

Duval–Valentin, "Specific inhibition of transcription by triple helix–forming oligonucleotides," *Proc. Natl. Acad. Sci. USA* 89:504–508 (Jan. 1992).

Eaton, "The joys in vitro selection: Chemically dressing oligonucleotides to satiate protein targets," *Curr. Opin. Chem. Biol.* 1:10–16 (Jun. 1997).

Egholm et al., "PNA hybridizes to complementary oligonucleotides obeying the Watson–Crick hydrogen–bonding rules," *Nature* 365:566–568 (Oct. 7, 1993).

Huang et al., "Mechanism of ribose 2' group discrimination by an RNA polymerase," *Biochemistry* 36:8231–8242 (1997).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (Issue No. 6, Jun. 1995).

Jarvis et al., "Inhibition of vascular smooth muscle cell proliferation by hammerhead ribozymes targeting c–myb," *Journal of Cellular Biochemistry* 19A:221 (1995) (Abstract Only).

Joyce et al., "Amplification, mutation and selection of catalytic RNA," *Gene* 82:83–87 (1989).

Joyce, "Choosing the right sugar: How polymerases select a nucleotide substrate," *Proc. Natl. Acad. Sci.* 94:1619–1622 (Issue No. 5, Mar. 4, 1997).

Joyce, "Directed Molecular Evolution," *Scientific American* 267:90–97 (Dec. 1992).

Kumar and Ellington, "Artificial evolution and natural ribozymes," *FASEB J.* 9:1183–1195 (Sep. 1995).

Lasic and Needham, "The 'Stealth' Liposome: A Prototypical Biomaterial," *Chemical Reviews* 95:2601–2627 (Issue No. 8, Dec. 1995).

Lasic and Papahadjopoulos, "Liposomes Revisited," *Science* 267:1275–1276 (Mar. 3, 1995).

Limbach et al., "Summary: the modified nucleosides of RNA," *Nucleic Acids Research* 22(12):2183–2196 (1994) (Issue No. 12).

Lin et al., "Modified RNA sequence pools for in vitro selection," *Nucleic Acids Research* 22:5229–5234 (Issue No. 24, Dec. 11, 1994).

Liu et al., "Cationic Liposome–mediated Intravenous Gene Delivery," *J. Biol. Chem.* 270(42):24864–24870 (Oct. 20, 1995).

Ludwig, "A simple one flask synthesis of nucleoside 5'–triphosphate from unprotected nucleosides via nucleoside 5'—cyclotriphosphates," Biophosphates and Their Analogues–Synthesis, Structure, Metabolism and Activity 201–204 (1987).

Ludwig, "A New Route to Nucleoside 5'–Triphosphates," *Acta. Biochim. Biophys. Acad. Sci. Hung.* 16:131–133 (1981) (Issue No. 3–4).

Ludwig and Eckstein, "Rapid and Efficient Synthesis of Nucleoside 5'–O–(1–Thiotriphosphates), 5'–Triphosphates and 2',3'–Cyclophosphorothioates Using 2–Chloro–4H–1,3, 2–Benzodioxaphosphorin–4–one," *J. Org. Chem.* 54:631–635 (1989).

Matulic–Adamic et al., "Synthesis of 3–(β–D–Ribofuranosyl)–2–fluoropyridine and 3–(β–D–Ribofuranosyl)–Pyridine–2–one," *Tetrahedron Letter* 38:203–206 (#2, Jan. 13, 1997).

Matulic–Adamic et al., "Synthesis of 3–(β–D–Ribofuranosyl)–Pyridin–2–one: A 'delection–modified' analogue of uridine," *Tetrahedron Letter* 38:1669–1672 (#10, Mar. 10, 1997).

Oku et al., "Real–Time analysis of liposomal trafficking in tumor–bearing mice by use of positron emission tomography," *Biochemica et Biophysica Acta* 1238:86–90 (1995).

Olsen et al., "Study of a Hammerhead Ribozyme Containing 2'–Modified Adenosine Residues," *Biochemistry* 30:9735–9741 (1991).

Sousa et al., "A mutant T7 RNA polymerase as a DNA polymerase," *EMBO J.* 14:4609–4621 (Issue No. 19, Sep. 15, 1995).

Stein and Cheng, "Antisense Oligonucleotides as Therapeutic Agents—Is the Bullet Really Magical?" *Science* 261:1004–1288 (Aug. 20, 1993).

Stull et al., "Antigene, Ribozyme and Aptamer Nucleic Acid Drugs: Progress and Prospects," *Pharmaceutical Research* 12:465–483 (1995) (Issue No. 4).

Szostak, "In Vitro Genetics," *TIBS* 17:89–93 (1993) (Mar. 1992).

Torrence et al., "Targeting RNA for degradation with a (2'–5') oligoadenylate antisense chimera," *Proc. Natl. Acad. Sci. USA* 90:1300–1304 (Feb. 1993).

Usman et al., "Hammerhead ribozyme engineering," *Current Opinion in Structural Biology* 1:527–533 (1996).

Wieczorek et al., "Evidence that total substitution of adenine with 7–deaza–adenine in the HDV antigenomic ribozyme changes the kinetics of RNA folding," *Bioorganic & Medicinal Chemistry Letters* 4:987–994 (1994) (Issue No. 8).

Williams et al., "Function of specific 2'–hydroxyl groups of guanosines in a hammerhead ribozyme probed by 2' modifications," *Proc. Natl. Acad. Sci. USA* 89:918–921 (1992).

\* cited by examiner

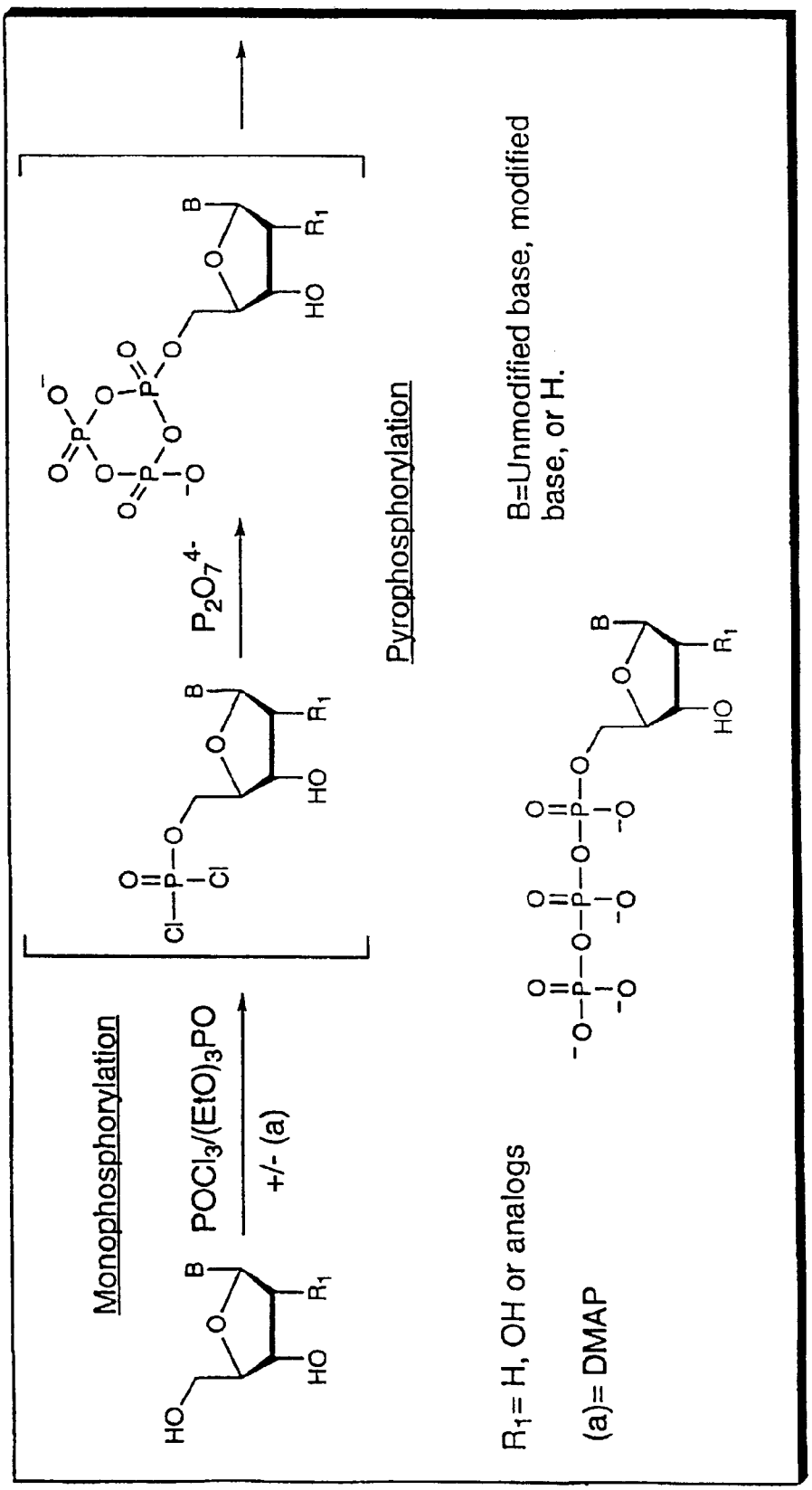
Fig. 1 One-Pot Formation of Nucleosides-5'-Triphosphates

NUCLEOSIDE TRIPHOSPHATES AND THEIR INCORPORATION INTO OLIGONUCLEOTIDES

CROSS-REFERENCE TO RELATED APPLICATIONS

This Application is a continuation of U.S. Ser. No. 09/186,675 by Beigelman et al., entitled "Nucleoside Triphosphates and Their Incorporation Into Oligonucleotides, filed Nov. 4, 1998, now U.S. Pat. No. 6,127,535, which claims the benefit of U.S. Provisional Application No. 60/064,866, entitled "Nucleoside Triphosphates and Their Incorporation Into Oligonucleotides," filed Nov. 5, 1997. These applications are incorporated by reference herein including any drawings, tables and figures.

BACKGROUND OF THE INVENTION

The following is a brief description of nucleoside triphosphates. This summary is not meant to be complete but is provided only for understanding of the invention that follows. This summary is not an admission that all of the work described below is prior art to the claimed invention.

The synthesis of nucleoside triphosphates and their incorporation into nucleic acids using polymerase enzymes has greatly assisted in the advancement of nucleic acid research. The polymerase enzyme utilizes nucleoside triphosphates as precursor molecules to assembly oligonucleotides. Each nucleotide is attached by a phosphodiester bond formed through nucleophilic attack by the 3' hydroxy group of the oligonucleotide's last nucleotide onto the 5' triphosphate of the next nucleotide. Nucleotides are incorporated one at a time into the oligonucleotide in a 5' to 3' direction. This process allows RNA to be produced and amplified from virtually any DNA or RNA templates.

Most natural polymerase enzymes incorporate standard nucleoside triphosphates into nucleic acid. For example, a DNA polymerase incorporates dATP, dTTP, dCTP, and dGTP into DNA and an RNA polymerase generally incorporates ATP, CTP, UTP, and GTP into RNA. There are however, certain polymerases that are capable of incorporating non-standard nucleoside triphosphates into nucleic acids (Joyce, 1997, *PNAS* 94, 1619–1622, Huang et al., *Biochemistry* 36, 8231–8242).

Before nucleosides can be incorporated into RNA transcripts using polymerase enzymes they must first be converted into nucleoside triphosphates which can be recognized by these enzymes. Phosphorylation of unblocked nucleosides by treatment with $POCl_3$ and trialkyl phosphates was shown to yield nucleoside 5'-phosphorodichloridates (Yoshikawa et al., 1969, *Bull. Chem. Soc.(Japan)* 42, 3505). Adenosine or 2'-deoxyadenosine 5'-triphosphate was synthesized by adding an additional step consisting of treatment with excess tri-n-butylammonium pyrophosphate in DMF followed by hydrolysis (Ludwig, 1981, *Acta Biochim. et Biophys. Acad. Sci. Hung.* 16, 131–133).

Non-standard nucleoside triphosphates are not readily incorporated into RNA transcripts by traditional RNA polymerases. Mutations have been introduced into RNA polymerase to facilitate incorporation of deoxyribonucleotides into RNA (Sousa & Padilla, 1995, *EMBO J.* 14,4609–4621, Bonner et al., 1992, *EMBO J.* 11, 3767–3775, Bonner et al., 1994, *J. Biol. Chem.* 42, 25120–25128, Aurup et al., 1992, *Biochemistry* 31, 9636–9641).

McGee et al., International PCT publication No. WO 95/35102, describes the incorporation of 2'-$NH_2$-NTP's, 2'-F-NTP's, and 2'-deoxy-2'-benzyloxyamino UTP into RNA using bacteriophage T7 polymerase.

Wieczorek et al., 1994, *Bioorganic & Medicinal Chemistry Letters* 4, 987–994, describes the incorporation of 7-deaza-adenosine triphosphate into an RNA transcript using bacteriophage T7 RNA polymerase.

Lin et al., 1994, *Nucleic Acids Research* 22, 5229–5234, reports the incorporation of 2'-$NH_2$-CTP and 2'-$NH_2$-UTP into RNA using bacteriophage T7 RNA polymerase and polyethylene glycol containing buffer. The article describes the use of the polymerase synthesized RNA for in vitro selection of aptamers to human neutrophil elastase (HNE).

SUMMARY OF THE INVENTION

This invention relates to novel nucleotide triphosphate (NTP) molecules, and their incorporation into nucleic acid molecules, including nucleic acid catalysts. The NTPs of the instant invention are distinct from other NTPs known in the art. The invention further relates to incorporation of these nucleoside triphosphates into oligonucleotides using an RNA polymerase; the invention further relates to novel transcription conditions for the incorporation of modified (non-standard) and unmodified NTP's into nucleic acid molecules. Further, the invention relates to methods for synthesis of novel NTP's.

In a first aspect, the invention features NTP's having the formula triphosphate-OR, for example the following formula I:

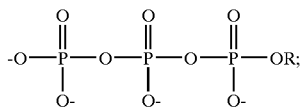

where R is any nucleoside; specifically the nucleosides 2'-O-methyl-2,6-diaminopurine riboside;2'-deoxy-2'-amino-2,6-diaminopurine riboside;2'-(N-alanyl)amino-2'-deoxy-uridine; 2'-(N-phenylalanyl)amino-2'-deoxy-uridine;2'-deoxy-2'-(N-β-alanyl)amino; 2'-deoxy-2'-(lysiyl)amino uridine;2'-C-allyl uridine;2'-O-amino-uridine;2'-O-methylthiomethyl adenosine; 2'-O-methylthiomethyl cytidine; 2'-O-methylthiomethyl guanosine;2'-O-methylthiomethyl-uridine;2'-Deoxy-2'-(N-histidyl)amino uridine; 2'-deoxy-2'-amino-5-methyl cytidine;2'-(N-β-carboxamidine-β-alanyl)amino-2'-deoxy-uridine; 2'-deoxy-2'-(N-β-alanyl)-guanosine; and 2'-O-amino-adenosine.

In a second aspect, the invention features a process for the synthesis of pyrimidine nucleotide triphosphate (such as UTP, 2'-O-MTM-UTP, dUTP and the like) including the steps of monophosphorylation where the pyrimidine nucleoside is contacted with a mixture having a phosphorylating agent (such as phosphorus oxychloride, phospho-tris-triazolides, phospho-tris-triimidazolides and the like), trialkyl phosphate (such as triethylphosphate or trimethylphosphate or the like) and dimethylaminopyridine (DMAP) under conditions suitable for the formation of pyrimidine monophosphate; and pyrophosphorylation where the pyrimidine monophosphate is contacted with a pyrophosphorylating reagent (such as tributylammonium pyrophosphate) under conditions suitable for the formation of pyrimidine triphosphates.

The term "nucleotide" as used herein is as recognized in the art to include natural bases (standard), and modified bases well known in the art. Such bases are generally located at the 1' position of a sugar moiety. Nucleotides generally include a base, a sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art as recently summarized by Limbach et al., 1994, *Nucleic Acids Res.* 22, 2183. some of the non-limiting examples of base modifications that can be introduced into nucleic acids without significantly effecting their catalytic activity include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azopyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine and uracil at 1' position or their equivalents; such bases may be used within the catalytic core of an enzymatic nucleic acid molecule and/or in the substrate-binding regions of such a molecule. Such modified nucleotides include dideoxynucleotides which have pharmaceutical utility well known in the art, as well as utility in basic molecular biology methods such as sequencing.

By "unmodified nucleoside" is meant one of the bases adenine, cytosine, guanine, uracil joined to the 1' carbon of β-D-ribo-furanose.

By "modified nucleoside" is meant any nucleotide base which contains a modification in the chemical structure of an unmodified nucleotide base, sugar and/or phosphate.

By "pyrimidines" is meant nucleotides comprising modified or unmodified derivatives of a six membered pyrimidine ring. An example of a pyrimidine is modified or unmodified uridine.

By "nucleotide triphosphate" of "NTP" is meant a nucleoside bound to three inorganic phosphate groups at the 5' hydroxyl group of the modified or unmodified ribose or deoxyribose sugar where the 1' position of the sugar may comprise a nucleic acid base or hydrogen. The triphosphate portion may be modified to include chemical moieties which do not destroy the functionality of the group (i.e., allow incorporation into an RNA molecule).

In another preferred embodiment, nucleoside triphosphates (NTP's) of the instant invention are incorporated into an oligonucleotide using an RNA polymerase enzyme. RNA polymerases include but are not limited to mutated and wild type versions of bacteriophage T7, SP6, or T3 RNA polymerases.

In yet another preferred embodiment, the invention features a process for incorporating modified NTP's into an oligonucleotide including the step of incubating a mixture having a DNA template, RNA polymerase, NTP, and an enhancer of modified NTP incorporation under conditions suitable for the incorporation of the modified NTP into the oligonucleotide.

By "enhancer of modified NTP incorporation" is meant a reagent which facilitates the incorporation of modified nucleotides into a nucleic acid transcript by an RNA polymerase. Such reagents include but are not limited to methanol; LiCl; polyethylene glycol (PEG); diethyl ether; propanol; methyl amine; ethanol and the like.

In another preferred embodiment, the modified nucleoside triphosphates can be incorporated by transcription into a nucleic acid molecules including enzymatic nucleic acid, antisense, 2–5A antisense chimera, oligonucleotides, triplex forming oligonucleotide (TFO), aptamers and the like (Stull et al., 1995 *Pharmaceutical Res.* 12, 465).

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004; Agrawal et al., U.S. Pat. No. 5,591,721; Agrawal, U.S. Pat. No. 5,652,356).

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "oligonucleotide" as used herein is meant a molecule having two or more nucleotides. The polynucleotide can be single, double or multiple stranded and may have modified or unmodified nucleotides or non-nucleotides or various mixtures and combinations thereof.

By "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme, finderon or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule.

By "enzymatic portion" or "catalytic domain" is meant that portion/region of the ribozyme essential for cleavage of a nucleic acid substrate.

By "substrate binding arm" or "substrate binding domain" is meant that portion/region of a ribozyme which is complementary to (i.e., able to base-pair with) a portion of its substrate. Generally, such complementarity is 100%, but can be less if desired. For example, as few as 10 bases out of 14 may be base-paired. That is, these arms contain sequences within a ribozyme which are intended to bring ribozyme and target together through complementary base-pairing interactions. The ribozyme of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If a ribozyme with two binding arms are chosen, then the length of the binding arms are symmetrical (i.e., each of the binding arms is of the same length; e.g., six and six nucleotides or seven and seven nucleotides long) or asymmetrical (i.e., the binding arms are of different length; e.g., six and three nucleotides or three and six nucleotides long).

By "nucleic acid molecule" as used herein is meant a molecule having nucleotides. The nucleic acid can be single, double or multiple stranded and may comprise modified or unmodified nucleotides or non-nucleotides or various mixtures and combinations thereof. An example of a nucleic acid molecule according to the invention is a gene which encodes for macromolecule such as a protein.

By "complementarity" as used herein is meant a nucleic acid that can form hydrogen bond(s) with other nucleic acid sequence by either traditional Watson-Crick or other non-traditional types (for example, Hoogsteen type) of base-paired interactions.

In yet another preferred embodiment, the modified nucleoside triphosphates of the instant invention can be used for combinatorial chemistry or in vitro selection of nucleic acid molecules with novel function. Modified oligonucleotides can be enzymatically synthesized to generate libraries for screening.

In yet another preferred embodiment, the invention features a process for the incorporating a plurality of compounds of formula I.

DESCRIPTION OF THE PREFERRED EMBODIMENTS

The drawings will first briefly be described.
Drawings:
FIG. 1 displays a schematic representation of NTP synthesis using nucleoside substrates.
Nucleotide Synthesis Addition of dimethylaminopyridine (DMAP) to the phosphorylation protocols known in the art can greatly increase the yield of nucleoside monophosphates while decreasing the reaction time (FIG. 1). Synthesis of the nucleosides of the invention have been described in several publications and Applicants previous applications (Beigelman et al., International PCT publication No. WO 96/18736; Dudzcy et al., Int. PCT Pub. No. WO 95/11910; Usman et al., Int. PCT Pub. No. WO 95/13378; Matulic-Adamic et al., 1997, Tetrahedron Lett. 38, 203; Matulic-Adamic et al., 1997, *Tetrahedron Lett.* 38, 1669; all of which are incorporated herein by reference). These nucleosides are dissolved in triethyl phosphate and chilled in an ice bath. Phosphorus oxychloride (POCl$_3$) is then added followed by the introduction of DMAP. The reaction is then warmed to room temperature and allowed to proceed for 5hours. This reaction allows the formation of nucleoside monophosphates which can then be used in the formation of nucleoside triphosphates. Tributylamine is added followed by the addition of anhydrous acetonitrile and tributylammonium pyrophosphate. The reaction is then quenched with TEAB and stirred overnight at room temperature (about 20 C.). The triphosphate is purified using column purification and HPLC and the chemical structure is confirmed using NMR analysis. Those skilled in the art will recognize that the reagents, temperatures of the reaction, and purification methods can easily be alternated with substitutes and equivalents and still obtain the desired product.

Nucleoside Triphosphates

The invention provides nucleoside triphosphates which can be used for a number of different functions. The nucleoside triphosphates formed from nucleosides found in table I are unique and distinct from other nucleoside triphosphates known in the art. Incorporation of modified nucleotides into DNA or RNA oligonucleotides can alter the properties of the molecule. For example, modified nucleotides can hinder binding of nucleases, thus increasing the chemical half-life of the molecule. This is especially important if the molecule is to be used for cell culture or in vivo. It is known in the art that the introduction of modified nucleotides into these molecules can greatly increase the stability and thereby the effectiveness of the molecules (Burgin et al., 1996, *Biochemistry* 35, 14090–14097; Usman et al., 1996, *Curr. Opin. Struct. Biol.* 6, 527–533).

Modified nucleotides are incorporated using either wild type and mutant polymerases. For example, mutant T7 polymerase is used in the presence of modified nucleotide triphosphate(s), DNA template and suitable buffers. Those skilled in the art will recognize that other polymerases and their respective mutant versions can also be utilized for the incorporation of NTP's of the invention. Nucleic acid transcripts were detected by incorporating radiolabelled nucleotides ($\alpha$-$^{32}$P NTP). The radiolabeled NTP contained the same base as the modified triphosphate being tested. The effects of methanol, PEG and LiCl were tested by adding these compounds independently or in combination. Detection and quantitation of the nucleic acid transcripts was performed using a Molecular Dynamics PhosphorImager. Efficiency of transcription was assessed by comparing modified nucleotide triphosphate incorporation with all-ribonucleotide incorporation control. Wild type polymerase was used to incorporate NTP's using the manufacturers buffers and instructions (Boehringer Mannheim).

Transcription Conditions

Incorporation rates of modified nucleoside triphosphates into oligonucleotides can be increased by adding to traditional buffer conditions, several different enhancers of modified NTP incorporation. Applicant has utilized methanol and LiCl in an attempt to increase incorporation rates of dNTP using RNA polymerase. These enhancers of modified NTP incorporation can be used in different combinations and ratios to optimize transcription. Optimal reaction conditions differ between nucleoside triphosphates and can readily be determined by standard experimentation. Overall however, inclusion of enhancers of modified NTP incorporation such as methanol or inorganic compound such as lithium chloride, have been shown by the applicant to increase the mean transcription rates.

Administration of Nucleoside mono, di or triphosphates

The nucleotide monophosphates, diphosphates, or triphosphates can be used as a therapeutic agent either independently or in combination with other pharmaceutical components. These molecules of the inventions can be administered to patients using the methods of Sullivan et al., PCT WO 94/02595. Molecules of the invention may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the modified nucleotide triphosphate, diphosphate or monophosphate/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged nucleotide mono, di or triphosphates of the invention can be administered and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., ammonium, sodium, calcium, magnesium, lithium, and potassium salts.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., NTP's, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of the a composition comprising surface-modified liposomes containing poly (ethylene glycol) lipids (PEG-modified, or long-circulating liposomes or stealth liposomes). These formulations offer an method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwataet al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). The long-circulating liposomes enhance the pharmacokinetics and pharmacodynamics of drugs, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by referenceherein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used.

By "patient" is meant an organism which is a donor or recipient of explanted cells or the cells themselves. "Patient" also refers to an organism to which the compounds of the invention can be administered. Preferably, a patient is a mammal, e.g., a human, primate or a rodent.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required.

EXAMPLES

The following are non-limiting examples showing the synthesis, incorporation and analysis of nucleoside triphosphates of the instant invention.

Applicant synthesized pyrimidine nucleoside triphosphates using DMAP in the reaction. For purines, applicant utilized standard protocols previously described in the art (Yoshikawa et al supra; Ludwig, supra). Described below is one example of a pyrimidine nucleotide triphosphate and one purine nucleotide triphosphate synthesis.

Example 1:
Synthesis of purine nucleoside triphosphates: 2'-O-methyl-guanosine-5'-triphosphate 2'-O-methyl guanosine nucleoside (0.25 grams, 0.84 mmol) was dissolved in triethyl phosphate (5.0) ml by heating to 100° C. for 5 minutes. The resulting clear, colorless solution was cooled to 0° C. using an ice bath under an argon atmosphere. Phosphorous oxychloride (1.8 eq., 0.141 ml) was then added to the reaction mixture with vigorous stirring. The reaction was monitored by HPLC, using a sodium perchlorate gradient. After 5 hours at 0° C., tributylamine (0.65 ml) was added followed by the addition of anhydrous acetonitrile (10.0 ml), and after 5 minutes (reequilibration to 0° C.) tributylammonium pyrophosphate (4.0 eq., 1.53 g) was added. The reaction mixture was quenched with 20 ml of 2M TEAB after 15 minutes at 0° C. (HPLC analysis with above conditions showed consumption of monophosphate at 10 minutes) then stirred overnight at room temperature, the mixture was evaporated in vacuo with methanol co-evaporation (4x) then diluted in 50 ml 0.05M TEAB. DEAE sephadex purification was used with a gradient of 0.05 to 0.6 M TEAB to obtain pure triphosphate (0.52 g, 66.0% yield) (elutes around 0.3M TEAB); the purity was confirmed by HPLC and NMR analysis.

Example 2:
Synthesis of Pyrimdine nucleoside triphosphates: 2'-O-methylthiomethyl-uridine-5'-triphosphate 2'-O-methylthiomethyl uridine nucleoside (0.27 grams, 1.0 mmol) was dissolved in triethyl phosphate (5.0 ml). The resulting clear, colorless solution was cooled to 0° C. with an ice bath under an argon atmosphere. Phosphorus oxychloride (2.0 eq., 0.190 ml) was then added to the reaction mixture with vigorous stirring. Dimethylaminopyridine (DMAP, 0.2 eq., 25 mg) was added, the solution warmed to room temperature and the reaction was monitored by HPLC, using a sodium perchlorate gradient. After 5 hours at 20° C., tributylamine (1.0 ml) was added followed by anhydrous acetonitrile (10.0 ml), and after 5 minutes tributylammonium pyrophosphate (4.0 eq., 1.8 g) was added. The reaction mixture was quenched with 20 ml of 2M TEAB after 15 minutes at 20° C. (HPLC analysis with above conditions showed consumption of monophosphate at 10 minutes) then stirred overnight at room temperature. The mixture was evaporated in vacuo with methanol co-evaporation (4x) then diluted in 50 ml 0.05M TEAB. DEAE fast flow Sepharose purification with a gradient of 0.05 to 1.0 M TEAB was used to obtain pure triphosphate (0.40 g, 4% yield) (elutes around 0.3M TEAB) as determined by HPLC and NMR analysis.

Example 3:
Utilization of DMAP in Uridine 5'-Triphosphate Synthesis

The reactions were performed on 20 mg aliquots of nucleoside dissolved in 1 ml of triethyl phosphate and 19 ul of phosphorus oxychloride. The reactions were monitored at 40 minute intervals automatically by HPLC to generate yield-of-product curves at times up to 18 hours. A reverse phase column and ammonium acetate/sodium acetate buffer system (50 mM & 100 mM respectively at pH 4.2) was used to separate the 5', 3', 2' monophosphates (the monophosphates elute in that order) from the 5'-triphosphate and the starting nucleoside. The data is shown in table 2. These conditions doubled the product yield and resulted in a 10-fold improvement in the reaction time to maximum yield (1200 minutes down to 120 minutes for a 90% yield). Selectivity for 5'-monophosphorylation was observed for all reactions. Subsequent triphosphorylation occurred in nearly quantitative yield.

Materials Used in Bacteriophage T7 RNA Polymerase Reactions

Buffer 1:
Reagents are mixed together to form a 10 X stock solution of buffer 1 (400 mM Tris-Cl (pH 8.1), 200 mM $MgCl_2$, 100 mM DTT, 50 mM spermidine, and 0.1% triton X-100. Prior to initiation of the polymerase reaction methanol, LiCl is added and the buffer is diluted such that the final reaction conditions for condition 1 consisted of: 40 mM tris pH (8.1), 20 mM $MgCl_2$, 10 mM DTT, 5 mM spermidine, 0.01% triton X-100, 10% methanol, and 1 mM LiCl.

Buffer 2:
Reagents are mixed together to form a 10 X stock solution of buffer 2(400 mM Tris-Cl (pH 8.1), 200 mM $MgCl_2$, 100 mM DTT, 50 mM spermidine, and 0.1% triton X-100. Prior to initiation of the polymerase reaction PEG, LiCl is added and the buffer is diluted such that the final reaction conditions for buffer 2 consisted of:40 mM tris pH (8.1), 20 mM $MgCl_2$, 10 mM DTT, 5 mM spermidine, 0.01% triton X-100, 4% PEG, and 1 mM LiCl.

Buffer 3:
Reagents are mixed together to form a 10 X stock solution of buffer 3 (400 mM Tris-Cl (pH 8.0), 120 mM $MgCl_2$, 50 mM DTT, 10 mM spermidine and 0.02% triton X-100. Prior to initiation of the polymerase reaction PEG is added and the buffer is diluted such that the final reaction conditions for buffer 3 consisted of:40 mM tris pH (8.0), 12 mM $MgCl_2$, 5 mM DTT, 1 mM spermidine, 0.002% triton X-100, and 4% PEG.

Buffer 4:
Reagents are mixed together to form a 10 X stock solution of buffer 4 (400 mM Tris-Cl (pH 8.0), 120 mM $MgCl_2$, 50 mM DTT, 10 mM spermidine and 0.02% triton X-100. Prior to initiation of the polymerase reaction PEG, methanol is added and the buffer is diluted such that the final reaction conditions for buffer 4 consisted of: 40 mM tris pH (8.0), 12 mM $MgCl_2$, 5 mM DTT, 1 mM spermidine, 0.002% triton X-100, 10% methanol, and 4% PEG.

Buffer 5:
Reagents are mixed together to form a 10 X stock solution of buffer 5 (400 mM Tris-Cl (pH 8.0), 120 mM $MgCl_2$, 50 mM DTT, 10 mM spermidine and 0.02% triton X-100. Prior to initiation of the polymerase reaction PEG, LiCl is added and the buffer is diluted such that the final reaction conditions for buffer 5 consisted of:40 mM tris pH (8.0), 12 mM $MgCl_2$, 5 mM DTT, 1 mM spermidine, 0.002% triton X-100, 1 mM LiCl and 4% PEG.

Buffer 6:
Reagents are mixed together to form a 10 X stock solution of buffer 6 (400 mM Tris-Cl (pH 8.0), 120 mM $MgCl_2$, 50 mM DTT, 10 mM spermidine and 0.02% triton X-100. Prior to initiation of the polymerase reaction PEG, methanol is added and the buffer is diluted such that the final reaction conditions for buffer 6 consisted of:40 mM tris pH (8.0), 12 mM $MgCl_2$, 5 mM DTT, 1 mM spermidine, 0.002% triton X-100, 10% methanol, and 4% PEG.

Example 4:

Screening of Modified Nucleoside triphosphates with Mutant T7 RNA Polymerase

Each modified nucleotide triphosphate was individually tested in buffers 1 through 6 at two different temperatures (25 and 37° C.). Buffers 1–6 tested at 25° C. were designated conditions 1–6 and buffers 1–6 test at 37° C. were designated conditions 7–12 (table 3). In each condition, Y639F mutant T7 polymerase (Sousa and Padilla, Supra) (0.3–2 mg/20 ml reaction), NTP's (2 mM each), DNA template (10 pmol), inorganic pyrophosphatase (5 U/ml) and $\alpha$-$^{32}$P.NTP (0.8 mCi/pmol template) were combined and heated at the designated temperatures for 1–2 hours. The radiolabeled NTP used was different from the modified triphosphate being testing. The samples were resolved by polyacrylamide gel electrophoresis. Using a phosphorImager (Molecular Dynamics, Sunnyvale, Calif.), the amount of full-length transcript was quantified and compared with an all-RNA control reaction. The data is presented in Table 4; results in each reaction is expressed as a percent compared to the all-ribonucleotide triphosphate (rNTP) control. The control was run with the mutant T7 polymerase using commercially available polymerase buffer (Boehringer Mannheim, Indianapolis, Ind.).

Example 5:

Incorporation of Modified NTP's using Wild-type T7 RNA polymerase

Bacteriophage T7 RNA polymerase was purchased from Boehringer Mannheim at 0.4 U/$\mu$L concentration. Applicant used the commercial buffer supplied with the enzyme and 0.2 $\mu$Ci alpha-$^{32}$P NTP in a 50 $\mu$L reaction with nucleotides triphosphates at 2 mM each. The template was double-stranded PCR fragment, which was used in previous screens. Reactions were carried out at 37° C. for 1 hour. 10 $\mu$L of the sample was run on a 7.5% analytical PAGE and bands were quantitated using a PhosphorImager. Results are calculated as a comparison to an "all ribo" control (non-modified nucleoside triphosphates) and the results are in Table 5.

Example 6:

Incorporation of Multiple Modified Nucleoside triphosphates Into Oligonucleotides Combinations of modified nucleoside triphosphates were tested with the transcription protocol described in example 4, to determine the rates of incorporation of two or more of these triphosphates. Incorporation 2'-Deoxy-2'-(L-histidine) amino uridine (2'-his-NH$_2$-UTP) was tested with unmodified cytidine nucleoside triphosphates, rATP and rGTP in reaction condition number 9. The data is presented as a percentage of incorporation of modified NTP's compared to the all rNTP control and is shown in Table 6a.

Two modified cytidines (2-'-NH$_2$-CTP or 2'dCTP) were incorporated along with 2'-his-NH$_2$-UTP with identical efficiencies. 2'-his-NH$_2$-UTP and 2'-NH$_2$-CTP were then tested with various unmodified and modified adenosine triphosphates in the same buffer (Table 6b). The best modified adenosine triphosphate for incorporation with both 2'-his-NH$_2$-UTP and 2'-NH$_2$-CTP was 2'-NH$_2$-DAPTP.

Example 7:

Optimization of Reaction conditions for Incorporation of Modified Nucleotide Triphosphate The combination of 2'-his-NH$_2$-UTP, 2'-NH$_2$-CTP, 2'-NH$_2$-DAP, and rGTP was tested in several reaction conditions (Table 7) using the incorporation protocol described in example 9. The results demonstrate that of the buffer conditions tested, incorporation of these modified nucleoside triphosphates occur in the presence of both methanol and LiCl.

Applications

The use of NTP's described in this invention have several research and commercial applications. These modified nucleoside triphosphates can be used for in vitro selection (evolution) of oligonucleotides with novel functions. Examples of in vitro selection protocols are incorporated herein by reference (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.*, 9, 1183; Breaker, 1996, *Curr. Op. Biotech.*, 7, 442).

Additionally, these modified nucleoside triphosphates can be employed to generate modified oligonucleotide combinatorial chemistry libraries. Several references for this technology exist (Brenner et al., 1992, *PNAS* 89, 5381–5383, Eaton, 1997, *Curr. Opin. Chem. Biol.* 1, 10–16) which are all incorporated herein by reference.

Other embodiments are within the following claims.

TABLE 1

NUCLEOSIDES USED FOR CHEMICAL SYNTHESIS
OF MODIFIED NUCLEOTIDE TRIPHOSPHATES

| | NUCLEOSIDES | Abbreviation | CHEMICAL STRUCTURE |
|---|---|---|---|
| 1 | 2'-O-methyl-2,6-diaminopurine riboside | 2'-O-Me-DAP | 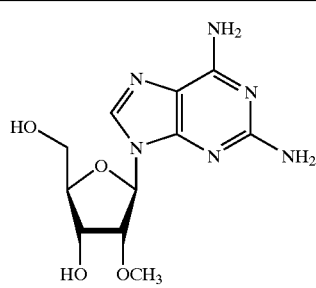 |

TABLE 1-continued

NUCLEOSIDES USED FOR CHEMICAL SYNTHESIS
OF MODIFIED NUCLEOTIDE TRIPHOSPHATES

| | NUCLEOSIDES | Abbreviation | CHEMICAL STRUCTURE |
|---|---|---|---|
| 2 | 2'-deoxy-2'amino-2,6-diaminopurine riboside | 2'-NH$_2$-DAP | 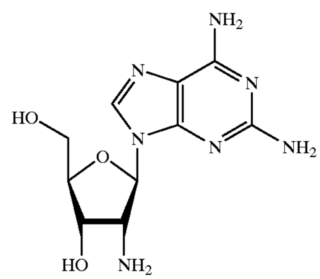 |
| 3 | 2'-(N-alanyl)amino-2'-deoxy-uridine | ala-2'-NH$_2$ U | 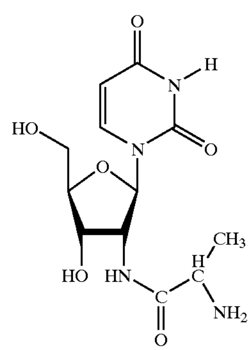 |
| 4 | 2'-(N-phenylalanyl)amino-2'-deoxy-uridine | phe-2'-NH$_2$-U | 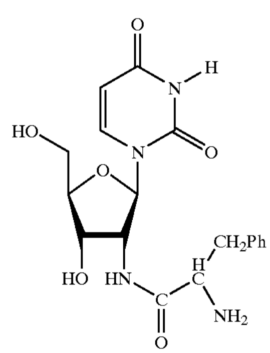 |
| 5 | 2'-(N-β-alanyl)amino-2'-deoxy uridine | 2'-β-Ala-NH$_2$-U | 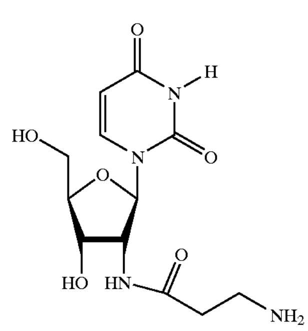 |

TABLE 1-continued

NUCLEOSIDES USED FOR CHEMICAL SYNTHESIS
OF MODIFIED NUCLEOTIDE TRIPHOSPHATES

| | NUCLEOSIDES | Abbreviation | CHEMICAL STRUCTURE |
|---|---|---|---|
| 6 | 2'-Deoxy-2'-(lysiyl) amino uridine | 2'-L-lys-NH$_2$-U | |
| 7 | 2'-C-allyl uridine | 2'-C-allyl-U | |
| 8 | 2'-O-amino-uridine | 2'-O-NH$_2$-U | |
| 9 | 2'-O-methylthiomethyl adenosine | 2'-O-MTM-A | |

TABLE 1-continued
NUCLEOSIDES USED FOR CHEMICAL SYNTHESIS
OF MODIFIED NUCLEOTIDE TRIPHOSPHATES
| NUCLEOSIDES | Abbreviation | CHEMICAL STRUCTURE |
| --- | --- | --- |
| 10 2'-O-methylthiomethyl cytidine | 2'-O-MTM-C | 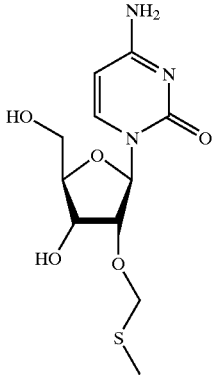 |
| 11 2'-O-methylthiomethyl guanosine | 2'-O-MTM-G | 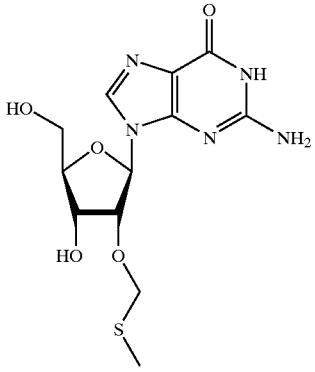 |
| 12 2'-O-methylthiomethyl-uridine | 2'-O-MTM-U | 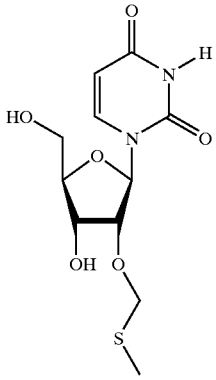 |

TABLE 1-continued
NUCLEOSIDES USED FOR CHEMICAL SYNTHESIS
OF MODIFIED NUCLEOTIDE TRIPHOSPHATES
| NUCLEOSIDES | Abbreviation | CHEMICAL STRUCTURE |
|---|---|---|
| 13 2'-(N-histidyl) amino uridine | 2'-his-NH$_2$-U | 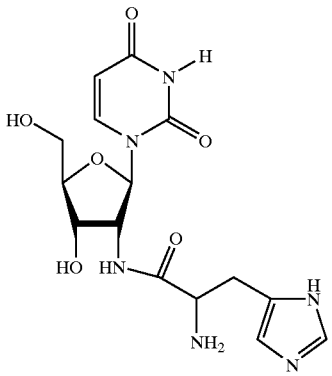 |
| 14 2'-Deoxy-2'-amino-5-methyl cytidine | 5-Me-2'-NH$_2$-C | 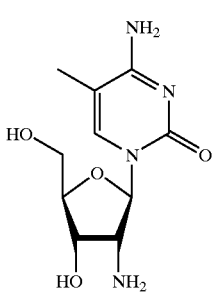 |
| 15 2'-(N-β-carboxamidine-β-alanyl)amino-2'-deoxy-uridine | β-ala-CA-NH2-U | 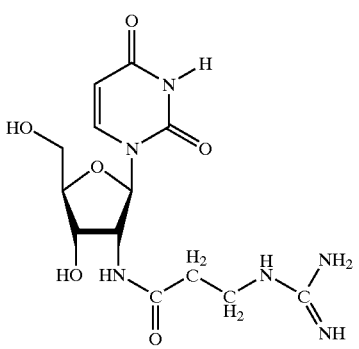 |
| 16 2'-(N-β-alanyl) guanosine | β-Ala-NH$_2$-G | 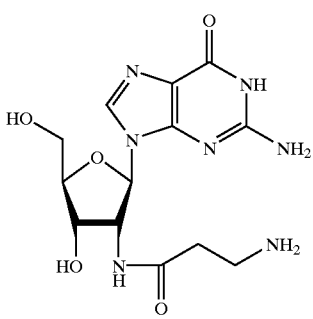 |

TABLE 1-continued

NUCLEOSIDES USED FOR CHEMICAL SYNTHESIS OF MODIFIED NUCLEOTIDE TRIPHOSPHATES

| NUCLEOSIDES | Abbreviation | CHEMICAL STRUCTURE |
|---|---|---|
| 17 2'-O-Amino-Adenosine | 2'-O-$NH_2$-A | 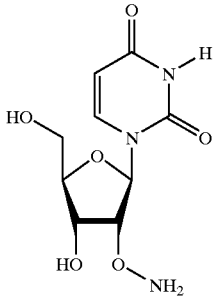 |

TABLE 2

PHOSPHORYLATION OF URIDINE IN THE PRESENCE OF DMAP

| 0 equiv. DMAP | | 0.2 equiv. DMAP | | 0.5 equiv. DMAP | | 1.0 equiv. DMAP | |
|---|---|---|---|---|---|---|---|
| Time (min) | Product % | Time (min) | Product % | Time (min) | Product % | Time (min) | Product % |
| 0 | 1 | 0 | 0 | 0 | 0 | 0 | 0 |
| 40 | 7 | 10 | 8 | 20 | 27 | 30 | 74 |
| 80 | 10 | 50 | 24 | 60 | 46 | 70 | 77 |
| 120 | 12 | 90 | 33 | 100 | 57 | 110 | 84 |
| 160 | 14 | 130 | 39 | 140 | 63 | 150 | 83 |
| 200 | 17 | 170 | 43 | 180 | 63 | 190 | 84 |
| 240 | 19 | 210 | 47 | 220 | 64 | 230 | 77 |
| 320 | 20 | 250 | 48 | 260 | 68 | 270 | 79 |
| 1130 | 48 | 290 | 49 | 300 | 64 | 310 | 77 |
| 1200 | 46 | 1140 | 68 | 1150 | 76 | 1160 | 72 |
| | | 1210 | 69 | 1220 | 76 | 1230 | 74 |

TABLE 3

Detailed Description of the NTP Incorporation Reaction Conditions

| Condition No. | TRIS-HCL (mM) | $MgCl_2$ (mM) | DTT (mM) | Spermidine (mM) | Triton X-100 (%) | METHANOL (%) | LiCl (mM) | PEG (%) | Temp (° C.) |
|---|---|---|---|---|---|---|---|---|---|
| 1 | 40 (pH 8.0) | 20 | 10 | 5 | 0.01 | 10 | 1 | — | 25 |
| 2 | 40 (pH 8.0) | 20 | 10 | 5 | 0.01 | 10 | 1 | 4 | 25 |
| 3 | 40 (pH 8.1) | 12 | 5 | 1 | 0.002 | — | — | 4 | 25 |
| 4 | 40 (pH 8.1) | 12 | 5 | 1 | 0.002 | 10 | — | 4 | 25 |
| 5 | 40 (pH 8.1) | 12 | 5 | 1 | 0.002 | — | 1 | 4 | 25 |
| 6 | 40 (pH 8.1) | 12 | 5 | 1 | 0.002 | 10 | 1 | 4 | 25 |
| 7 | 40 (pH 8.0) | 20 | 10 | 5 | 0.01 | 10 | 1 | — | 37 |
| 8 | 40 (pH 8.0) | 20 | 10 | 5 | 0.01 | 10 | 1 | 4 | 37 |
| 9 | 40 (pH 8.1) | 12 | 5 | 1 | 0.002 | — | — | 4 | 37 |
| 10 | 40 (pH 8.1) | 12 | 5 | 1 | 0.002 | 10 | — | 4 | 37 |
| 11 | 40 (pH 8.1) | 12 | 5 | 1 | 0.002 | — | 1 | 4 | 37 |
| 12 | 40 (pH 8.1) | 12 | 5 | 1 | 0.002 | 10 | 1 | 4 | 37 |

TABLE 4

INCORPORATION OF MODIFIED NUCLEOTIDE TRIPHOSPHATES

| Modification | COND #1 | COND #2 | COND #3 | COND #4 | COND #5 | COND #6 | COND #7 | COND #8 | COND #9 | COND #10 | COND #11 | COND #12 |
|---|---|---|---|---|---|---|---|---|---|---|---|---|
| 2'-$NH_2$-ATP | 1 | 2 | 3 | 5 | 2 | 4 | 1 | 2 | 10 | 11 | 5 | 9 |
| 2'-$NH_2$-CTP | 11 | 37 | 45 | 64 | 25 | 70 | 26 | 54 | 292 | 264 | 109 | 244 |

TABLE 4-continued

INCORPORATION OF MODIFIED NUCLEOTIDE TRIPHOSPHATES

| Modification | COND #1 | COND #2 | COND #3 | COND #4 | COND #5 | COND #6 | COND #7 | COND #8 | COND #9 | COND #10 | COND #11 | COND #12 |
|---|---|---|---|---|---|---|---|---|---|---|---|---|
| 2'-NH$_2$-GTP | 4 | 7 | 6 | 14 | 5 | 17 | 3 | 16 | 10 | 21 | 9 | 16 |
| 2'-NH$_2$-UTP | 14 | 45 | 4 | 100 | 85 | 82 | 48 | 88 | 20 | 418 | 429 | 440 |
| 2'-dATP | 9 | 3 | 19 | 23 | 9 | 24 | 6 | 3 | 84 | 70 | 28 | 51 |
| 2'-dCTP | 1 | 10 | 43 | 46 | 35 | 47 | 27 | 127 | 204 | 212 | 230 | 235 |
| 2'-dGTP | 6 | 10 | 9 | 15 | 9 | 12 | 8 | 34 | 38 | 122 | 31 | 46 |
| 2'-dTTP | 9 | 9 | 14 | 18 | 13 | 18 | 8 | 15 | 116 | 114 | 59 | 130 |
| 2'-O—Me-ATP | 0 | 0 | 0 | 0 | 0 | 0 | 1 | 1 | 2 | 2 | 2 | 2 |
| 2'-O—Me-CTP | no data compared to ribo; incorporates at low level | | | | | | | | | | | |
| 2'-O—Me-GTP | 4 | 3 | 4 | 4 | 4 | 4 | 2 | 4 | 4 | 5 | 4 | 5 |
| 2'-O—Me-UTP | 55 | 52 | 39 | 38 | 41 | 48 | 55 | 71 | 93 | 103 | 81 | 77 |
| 2'-O—Me-DAP | 4 | 4 | 3 | 4 | 4 | 5 | 4 | 3 | 4 | 5 | 5 | 5 |
| 2'-NH$_2$-DAP | 0 | 0 | 1 | 1 | 1 | 1 | 1 | 0 | 0 | 0 | 0 | 0 |
| ala-2'-NH$_2$-UTP | 2 | 2 | 2 | 2 | 3 | 4 | 14 | 18 | 15 | 20 | 13 | 14 |
| phe-2'-NH$_2$-UTP | 8 | 12 | 7 | 7 | 8 | 8 | 4 | 10 | 6 | 6 | 10 | 6 |
| 2'-β NH$_2$-ala-UTP | 65 | 48 | 25 | 17 | 21 | 21 | 220 | 223 | 265 | 300 | 275 | 248 |
| 2'-F-ATP | 227 | 252 | 98 | 103 | 100 | 116 | 288 | 278 | 471 | 198 | 317 | 185 |
| 2'-F-GTP | 39 | 44 | 17 | 30 | 17 | 26 | 172 | 130 | 375 | 447 | 377 | 438 |
| 2'-C-allyl-UTP | 3 | 2 | 2 | 3 | 3 | 2 | 3 | 3 | 3 | 2 | 3 | 3 |
| 2'-O—NH$_2$-UTP | 6 | 8 | 5 | 5 | 4 | 5 | 16 | 23 | 24 | 24 | 19 | 24 |
| 2'-O-MTM-ATP | 0 | 1 | 0 | 0 | 0 | 0 | 1 | 0 | 0 | 0 | 0 | 0 |
| 2'-O-MTM-CTP | 2 | 2 | 1 | 1 | 1 | 1 | 3 | 4 | 5 | 4 | 5 | 3 |
| 2'-O-MTM-GTP | 6 | 1 | 1 | 3 | 1 | 2 | 0 | 1 | 1 | 3 | 1 | 4 |

TABLE 5

INCORPORATION OF MODIFIED NUCLEOTIDE TRIPHOSPHATES USING WILD TYPE BACTERIOPHAGE T7 POLYMERASE

| Modification | label | % ribo control |
|---|---|---|
| 2'-NH$_2$-GTP | ATP | 4% |
| 2'-dGTP | ATP | 3% |
| 2'-O-Me-GTP | ATP | 3% |
| 2'-F-GTP | ATP | 4% |
| 2'-O-MTM-GTP | ATP | 3% |
| 2'-NH$_2$-UTP | ATP | 39% |
| 2'-dTTP | ATP | 5% |
| 2'-O-Me-UTP | ATP | 3% |
| ala-2'-NH$_2$-UTP | ATP | 2% |
| phe-2'-NH$_2$-UTP | ATP | 1% |
| 2'-β-ala-NH$_2$-UTP | ATP | 3% |
| 2'-C-allyl-UTP | ATP | 2% |
| 2'-O-NH$_2$-UTP | ATP | 1% |
| 2'-O-MTM-UTP | ATP | 64% |
| 2'-NH$_2$-ATP | GTP | 1% |
| 2'-O-MTM-ATP | GTP | 1% |
| 2'-NH$_2$-CTP | GTP | 59% |
| 2'-dCTP | GTP | 40% |

TABLE 6a

Incorporation of 2'-his-UTP and Modified CTP's

| modification | 2'-his-UTP | rUTP |
|---|---|---|
| CTP | 16.1 | 100 |
| 2'-amino-CTP | 9.5* | 232.7 |
| 2'-deoxy-CTP | 9.6* | 130.1 |
| 2'-OMe-CTP | 1.9 | 8.2 |
| 2'-MTM-CTP | 5.9 | 5.1 |
| control | 1.2 | |

TABLE 6b

Incorporation of 2'-his-UTP, 2-amino CTP, and Modified ATP's

| modification | 2'-his-UTP and 2'-amino-CTP | rUTP and rCTP |
|---|---|---|
| ATP | 15.7 | 100 |
| 2'-amino-ATP | 2.4 | 28.9 |
| 2'-deoxy-ATP | 2.3 | 146.3 |
| 2'-OMe-ATP | 2.7 | 15 |
| 2'-F-ATP | 4 | 222.6 |
| 2'-MTM-ATP | 4.7 | 15.3 |
| 2'-OMe-DAP | 1.9 | 5.7 |
| 2'-amino-DAP | 8.9* | 9.6 |

Numbers shown are a percentage of Incorporation compared to the all-RNA control
*Bold number indicates best observed rate of modified nucleotide triphosphate incorporation

TABLE 7

INCORPORATION OF 2'-his-UTP, 2'-NH$_2$-CTP, 2'-NH$_2$-DAP, and rGTP USING VARIOUS REACTION CONDITIONS

| Conditions | compared to all rNTP |
|---|---|
| 7 | 8.7* |
| 8 | 7* |
| 9 | 2.3 |
| 10 | 2.7 |
| 11 | 1.6 |
| 12 | 2.5 |

Numbers shown are a percentage of incorporation compared to the all-RNA control
*Two highest levels of incorporation contained both methanol and LiCl

What is claimed is:
1. A process for incorporation into an oligonucleotide a modified nucleotide triphosphate, comprising the step of contacting the modified nucleotide triphosphate with a mixture comprising a nucleic acid template, an RNA polymerase enzyme, and an enhancer of modified nucleotide triphosphate incorporation, under conditions suitable for the incorporation of the modified nucleotide triphosphate into said oligonucleotide.

2. The process of claim 1, wherein said RNA polymerase is a T7 RNA polymerase.

3. The process of claim 1, wherein said RNA polymerase is a mutant T7 RNA polymerase.

4. The process of claim 1, wherein said RNA polymerase is a SP6 RNA polymerase.

5. The process of claim 1, wherein said RNA polymerase is a mutant SP6 RNA polymerase.

6. The process of claim 1, wherein said RNA polymerase is a T3 RNA polymerase.

7. The process of claim 1, wherein said RNA polymerase is a mutant T3 RNA polymerase.

8. The process of claim 1, wherein said enhancer of modified nucleotide triphosphate incorporation is selected from the group consisting of LiCl, methanol, polyethylene glycol, diethyl ether, propanol, methylamine, and ethanol.

9. The process of claim 1, wherein said oligonucleotide is RNA.

10. The process of claim 1, wherein said oligonucleotide is an enzymatic nucleic acid molecule.

11. The process of claim 1, wherein said oligonucleotide is an aptamer.

12. The process of claim 1, wherein the modified nucleotide triphosphate comprises formula I:

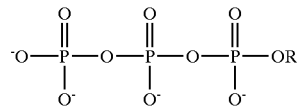

wherein R is independently a nucleoside attached through the 5'-position of its pentose moiety, wherein said nucleoside is selected from the group consisting of 2'-O-methyl-2,6-diaminopurine riboside; 2'-deoxy-2'-amino-2,6-diaminopurine riboside; 2'-(N-alanyl) amino-2'-deoxy-uridine; 2'-(N-phenylalanyl)amino-2'-deoxy-uridine; 2'-(N-β-alanyl) amino-2'-deoxy-uridine; 2'-(N-lysyl) amino-2'-deoxy-uridine; 2'-deoxy-2'-C-allyl uridine; 2'-O-amino-uridine; 2'-O-methylthiomethyl adenosine; 2'-O-methylthiomethyl cytidine; 2'-O-methylthiomethyl guanosine; 2'-O-methylthiomethyl uridine; 2'-(N-histidyl) amino-2'-deoxy-uridine; 2'-deoxy-2'-amino-5-methyl cytidine; 2'(N-β-alanyl)amino-2'-deoxy-guanosine; and 2'-O-amino-adenosine.

* * * * *